(12) United States Patent
Slupska et al.

(10) Patent No.: US 9,133,278 B2
(45) Date of Patent: Sep. 15, 2015

(54) METHODS FOR DETOXIFYING A LIGNOCELLULOSIC HYDROLYSATE

(71) Applicant: BP Corporation North America Inc., Houston, TX (US)

(72) Inventors: Malgorzata Slupska, San Diego, CA (US); Yukiko Sato, San Diego, CA (US); Karen Kustedjo, San Diego, CA (US); Kelvin Wong, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/765,039

(22) Filed: Feb. 12, 2013

(65) Prior Publication Data

US 2013/0210103 A1    Aug. 15, 2013

Related U.S. Application Data

(60) Provisional application No. 61/597,973, filed on Feb. 13, 2012.

(51) Int. Cl.
| | |
|---|---|
| C12P 7/00 | (2006.01) |
| C08B 15/00 | (2006.01) |
| C12P 7/10 | (2006.01) |
| C12N 1/22 | (2006.01) |
| D21C 1/06 | (2006.01) |
| D21C 3/02 | (2006.01) |
| D21C 5/00 | (2006.01) |

(52) U.S. Cl.
CPC . *C08B 15/00* (2013.01); *C12N 1/22* (2013.01); *C12P 7/10* (2013.01); *D21C 1/06* (2013.01); *D21C 3/02* (2013.01); *D21C 5/005* (2013.01); *Y02E 50/16* (2013.01)

(58) Field of Classification Search
CPC .................................. C12P 7/00; C12P 19/00
See application file for complete search history.

(56) References Cited

U.S. PATENT DOCUMENTS

| | | | | |
|---|---|---|---|---|
| 3,944,463 | A * | 3/1976 | Samuelson et al. | 162/65 |
| 5,366,558 | A | 11/1994 | Brink | |
| 6,423,145 | B1 * | 7/2002 | Nguyen et al. | 127/37 |
| 8,030,039 | B1 * | 10/2011 | Retsina et al. | 435/161 |
| 2011/0318798 | A1 | 12/2011 | Walther et al. | |
| 2013/0210084 | A1 | 8/2013 | Guerini et al. | |

FOREIGN PATENT DOCUMENTS

WO    WO2010/134455    11/2010

OTHER PUBLICATIONS

U.S. Appl. No. 13/764,943.*
B. Alriksson et al., Ammonium Hydroxide Detoxification of Spruce Acid Hydrolysates, Applied Biochemistry and Biotechnology vol. 121-124, 2005.
B. Alriksson et al., Optimal Conditions for Alkaline Detoxification of Dilute-Acid Hydrolysates, Applied Biochemistry and Biotechnology, vol. 129-132, 2006.
B. Alriksson et al., Improving the Fermentability of Enzymatic Hydrolysates of Lignoceliulose through Chemical in-situ Detoxification with Reducing Agents. Bioresource Technology 102 (2011) 1254-1263, www.elsevier.com/locate/biortech.
L. Jönsson et al., Bioconversion of Lignocellulose; inhibitors and detoxification; Biotechnology for Biofuels 2013, 6-16, www.biotechnologyforbiofuels.com/content/6/1/16.
I. Horvath et al., Critical Conditions for Improved Fermentabllity During Overliming of Acid Hydrolysates from Spruce, Applied Biochemistry and Biotechnology, vol. 121-124, 2005.
V. Soudham et al., Reducing agents Improve enzymatic hydrolysis of cellulosic substrates in the presence of pretreatment liquid, Journal of Biotechnology 155 (2011) 244-250.
J. Shen at al., Lime Treatment of Prehydrolysis Liquor from the Kraft-Based Dissolving Pulp Production Process, ACS Publications, 2011 American Chemical Society, 662-667.
J. Zhuang et al., Hydrolysis of Weath Straw Hemicellulose and Detoxification of the Hydrolysate for Xylitol Production, BioResources 4(2), 374-686 2009.

* cited by examiner

*Primary Examiner* — Ruth Davis
(74) *Attorney, Agent, or Firm* — DLA Piper LLP (US)

(57) ABSTRACT

The present disclosure relates to methods for detoxifying a hydrolysate obtained from a lignocellulosic biomass and methods of producing ethanol from the detoxified hydrolysate. The present methods provide detoxified hydrolysates in which the quantity of compounds that are deleterious to fermenting microorganisms are substantially reduced relative to the starting hydrolysate and in which the amount of fermentable sugars loss is minimal.

42 Claims, 5 Drawing Sheets

METHODS FOR DETOXIFYING A LIGNOCELLULOSIC HYDROLYSATE

1. BACKGROUND

Many industrial products are produced by microorganisms grown in culture. Microorganism growth may be supported by soluble sugar molecules released by lignocellulosic biomasses. Lignocellulosic biomasses consist primarily of cellulose (polymers of glucose linked by β-1,4-glucosidic bonds), hemicellulose (polysaccharide composed of different five (C5)—carbon sugars and six (C6)—carbon sugars linked by variety of different β and α linkages) and lignin (complex polymer consisting of phenyl propane units linked by ether or carbon-carbon bonds). In some cases, lignocellulosic biomasses are subject to dilute acid hydrolysis during which hemicellulose is hydrolyzed to monomeric sugars (liquid stream) and the crystalline structure of cellulose is damaged, facilitating future enzymatic digestion (solid fiber). The liquid containing C5 and C6 sugars, so called hydrolysate, is separated from cellulose and lignin solids and can be fermented to various products such as ethanol. In addition to sugars however, hydrolysate also contains aliphatic acids, esters (acetate), phenolics (different compounds obtained from lignin hydrolysis) and products of sugar dehydration, including the furan aldehydes furfural and 5-hydroxymethyl furfural (5-HMF). Most of these compounds have a negative impact on microorganisms and can inhibit fermentation. Detoxification of the hydrolysate prior to fermentation is one measure that can be taken in order to avoid inhibition caused by toxic compounds present in the hydrolysate.

Various methods of detoxification have been tested, with alkaline overliming being efficient and cost effective. During the overliming process, the pH of the hydrolysate is temporarily raised, usually at an elevated temperature, from a pH of approximately 2 to a pH of between 9 and 10 through the addition of an appropriate amount of calcium hydroxide (lime). After some time, typically about 30 minutes, the pH of the hydrolysate solution is lowered through the addition of acid to a pH suitable for fermenting microorganisms. In the detoxification process, furan aldehydes are degraded and acids (mineral and organic) are neutralized.

Overliming has been known for a long time (Leonard and Hajny, 1945, Ind. Eng. Chem., 37 (4):390-395) and still is considered an efficient detoxification method. However, a significant drawback of the method is the considerable amount of loss of fermentable sugars that occurs during detoxification. See, e.g., Larsson et al., 1999, Appl. Biochem. Biotechnol. 77-79:91-103. The loss of fermentable sugars results in lower overall yields of fermentable products such as ethanol. In addition, the formation of insoluble calcium sulfate (gypsum) during detoxification is problematic. See, e.g., Martinez et al., 2001, Biotechnol. Prog. 17(2):287-293. Gypsum formation causes fouling and pipeline clogging, which significantly drive up maintenance costs. To overcome problems associated with calcium hydroxide, other bases have been attempted for the purpose of hydrolysate detoxification, which have met with varying levels of success. See, e.g., Alriksson et al., 2005, Appl. Biochem. Biotechnol. 121-124: 911-922.

Accordingly, there is a need for new and improved processes to reduce fermentation inhibitors and detoxify hydrolysates obtained from lignocellulosic biomasses. In particular, there is a need for detoxification processes that are economically viable and provide detoxified hydrolysates capable of producing high yields of ethanol.

2. SUMMARY

The present disclosure stems from the discovery that magnesium bases (e.g., magnesium hydroxide, magnesium carbonate, or magnesium oxide) can effectively detoxify hydrolysates obtained from lignocellulosic biomasses (sometimes referred to herein as "lignocellulosic hydrolysates"), and that the detoxification process results in minimal losses of fermentable sugars. As used herein, the term "detoxification" refers to a process in which one or more compounds that are detrimental to a fermenting microorganism (referred to herein as "toxins") are removed from a starting lignocellulosic hydrolysate or inactivated, thereby forming a detoxified hydrolysate. As used herein, the phrase "detoxified hydrolysate" refers to a hydrolysate containing lower toxin levels than the toxin levels in the hydrolysate prior to the treatment with a magnesium base, referred to herein as a "starting hydrolysate". Such toxins include, but are not limited to, furan aldehydes, aliphatic acids, esters and phenolics.

Magnesium bases offer significant advantages over calcium hydroxide as detoxification bases. For instance, detoxification with magnesium bases results in less sugar burn than detoxification with calcium hydroxide. Additionally, detoxification with magnesium bases does not result in the production of insoluble byproducts that cause fouling and pipeline clogging which significantly drive up maintenance costs.

The hydrolysate detoxification methods of the present disclosure find application in the production of fuel molecules such as ethanol. When a hydrolysate is treated with a magnesium base for a sufficient time to remove or inactivate one or more toxins, the resultant detoxified lignocellulosic hydrolysate can be more effectively fermented by a fermenting microorganism (e.g., ethanologen) to produce a fermentation product such as ethanol. In exemplary embodiments involving ethanol fermentation, the quantity of ethanol generated by detoxified hydrolysates produced in accordance with the present disclosure is comparable to quantity of ethanol produced by hydrolysates that are detoxified with calcium hydroxide (see Example 5).

Accordingly, the disclosure generally provides methods of reducing the toxicity of a lignocellulosic hydrolysate towards a fermenting organism. In certain aspects, the methods involve mixing a solution of a starting hydrolysate (i.e., starting hydrolysate solution) with a magnesium base (e.g., magnesium hydroxide, magnesium carbonate or magnesium oxide) for a period of time and under conditions that result in the production of a solution of a detoxified hydrolysate (i.e., detoxified hydrolysate solution). The methods of the present disclosure provide detoxified hydrolysates in which the quantity of the toxins that are deleterious to fermenting microorganisms is substantially reduced relative to the starting hydrolysate. At the same time, the amount of fermentable sugars lost in the detoxification process is minimal.

In certain embodiments, the methods disclosed herein result in the production of a detoxified hydrolysate with at least 70%, at least 80%, at least 85%, at least 90%, at least 92%, at least 93%, at least 95% or at least 99% of the fermentable sugars present in the starting hydrolysate and no greater than 70%, no greater than 60%, no greater than 50%, no greater than 40%, no greater than 30%, no greater than 20% or no greater than 10% of the furan aldehydes present in the staring hydrolysate. In particular embodiments, detoxification methods of the present disclosure provide a detoxified hydrolysate with (a) at least 90% of the total fermentable sugars present in the starting hydrolysate and no greater than 50% of the furan aldehydes present in the starting hydrolysate; (b) at least 90% of the total fermentable sugars present in the starting hydrolysate and no greater than 40% of the furan aldehydes present in the starting hydrolysate; (c) at least 90% of the total fermentable sugars present in the starting hydrolysate and no greater than 30% of the furan aldehydes present in the starting hydrolysate; (d) at least 90% of the total fermentable sugars present in the starting hydrolysate and no greater than 20% of the furan aldehydes present in the starting hydrolysate; (e) at least 80% of the total fermentable sugars present in the starting hydrolysate and no greater than 50% of the furan aldehydes present in the starting hydrolysate; (f) at least 80% of the total fermentable sugars present in the starting hydrolysate and no greater than 40% of the furan aldehydes present in the starting hydrolysate; (g) at least 80% of the total fermentable sugars present in the starting hydrolysate and no greater than 30% of the furan aldehydes present in the starting hydrolysate; or (h) at least 80% of the total fermentable sugars present in the starting hydrolysate and no greater than 20% of the furan aldehydes present in the starting hydrolysate.

The biomass is preferably lignocellulosic and can include, without limitation, seeds, grains, tubers, plant waste or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), wood (including, e.g., wood chips, processing waste), paper, pulp, and recycled paper (including, e.g., newspaper, printer paper, and the like). Other biomass materials include, without limitation, potatoes, soybean (e.g., rapeseed), barley, rye, oats, wheat, beets, and sugar cane bagasse. Further sources of biomass are disclosed in Section 4.1 and can be used in the present methods.

The concentration of the individual compounds of the hydrolysate in the hydrolysate solution prior to detoxification depends, in part, on the biomass from with the hydrolysate is obtained and the method used to hydrolyze the biomass, as well as hydrolysis conditions. In certain embodiments, the starting hydrolysate solution comprises (a) fermentable sugars at a concentration ranging from 30 g/L to 160 g/L, from 40 g/L to 95 g/L, or from 50 g/L to 70 g/L; (b) furfural at a concentration ranging from 0.5 g/L to 10 g/L, from 2.5 g/L to 4 g/L, or from 1.5 g/L to 5 g/L; (c) 5-HMF at a concentration ranging from 0.1 g/L to 5 g/L, from 0.5 g/L to 2.5 g/L or from 1 g/L to 2 g/L; (d) acetic acid at a concentration ranging from 2 g/L to 17 g/L or from 11 g/L to 16 g/L; (e) lactic acid at a concentration ranging from 0 g/L to 12 g/L or from 4 g/L to 10 g/L; (f) additional aliphatic acids (e.g., succinic acid, formic acid, butyric acid and levulinic acid) at concentrations ranging from 0 g/L to 2.5 g/L; and/or (g) phenolics at a concentration ranging from 0 g/L to 10 g/L, from 0.5 g/L to 5 g/L or from 1 g/L to 3 g/L.

The starting hydrolysate solution can be concentrated prior to detoxification. For instance, following biomass hydrolysis, a hydrolysate solution can be concentrated by 1.2-fold, 1.5-fold, 2-fold, 3-fold or 5-fold. In specific embodiments, the starting hydrolysate is concentrated in a range bounded by any two of the foregoing embodiments, e.g., concentrated in the range from 1-fold to 3-fold, 1.5-fold to 3-fold, 3-fold to 5-fold, etc.

In various embodiments, the detoxification of the lignocellulosic hydrolysate solution can be carried out at a temperature ranging from 25° C. to 90° C. The detoxification process can be carried out, for example at 30° C., 35° C., 40° C., 45° C., 50° C., 55° C., 60° C., 65° C., 70° C., 75° C., 80° C., 85° C., or 90° C. In specific embodiments, the detoxification process is carried out at a temperature in the range bounded by any two of the foregoing temperatures, e.g., at a temperature ranging from 40° C. to 60° C., from 45° C. to 50° C., from 35° C. to 65° C., etc. Advantageously, the detoxification process is carried out at a temperature ranging from 40° C. to 60° C., which allows the detoxification reactions to occur at a commercially feasible rate while minimizing the loss of fermentable sugars, and thereby increasing the yield of fermentation products (e.g., ethanol, biochemicals).

The hydrolysate detoxification process is typically carried out at a pH ranging from 6.2 to 9.5. For instance, the detoxification can be carried out at a pH of 6.5, 7, 7.5, 8, 8.5, 9, or 9.5. In specific embodiments, the detoxification process can be carried out at a pH in the range bounded by any two of the foregoing values, e.g., at a pH ranging from 6.5 to 8, from 7 to 8, etc.

In certain aspects, the disclosure provides for a method of reducing the toxicity of a lignocellulosic hydrolysate towards a fermenting organism, comprising the step of mixing a starting lignocellulosic hydrolysate solution, said starting lignocellulosic hydrolysate solution comprising a mixture of fermentable sugars, furan aldehydes and aliphatic acids, with a magnesium base for a period of time of at least 1 hour, at least 4 hours, at least 10 hours or at least 20 hours at a temperature between 40° C. and 70° C. and at a pH of between 6.5 and 8. In particular embodiments, the magnesium base is magnesium hydroxide.

The detoxification process can be carried out as a batch process, as a continuous process, or as a semi-continuous process. The detoxification process can be carried out in a batch reactor, a continuous stirred tank reactor (CSTR), a series of continuous stirred tank reactors, or a plug flow reactor (PFR).

The disclosure further provides methods for continuously reducing the quantity of toxins in a hydrolysate, comprising the steps of flowing a first continuous stream of a hydrolysate into a continuous reactor or a series of continuous reactors, flowing a second continuous stream of a solution of a magnesium base into the continuous reactor or the series of continuous reactors, mixing the hydrolysate with the magnesium base in the continuous reactor for a period of time sufficient to reduce the quantity of toxins in the hydrolysate, and flowing the hydrolysate out of the continuous reactor.

The detoxified hydrolysates of the present disclosure can be fermented by a fermenting microorganism to produce fermentation products such as ethanol. Accordingly, the methods of the disclosure further include culturing a fermenting microorganism in the presence of a detoxified hydrolysate produced in accordance with the present disclosure under conditions in which a fermentation product is produced. Various fermenting microorganisms (e.g., ethanologens) can be used to produce fermentation products such as those described in Section 4.5.

Additionally, the disclosure provides methods for continuously producing a fermentation product, comprising flowing a first continuous stream of a hydrolysate into a continuous reactor or a series of continuous reactors or the series of continuous reactors, flowing a second continuous stream of a magnesium base into the continuous reactor, mixing the hydrolysate with the magnesium base in the continuous reactor for a period of time sufficient to detoxify (i.e., reduce the quantity) of toxins in the hydrolysate, flowing the hydrolysate out of the continuous reactor, reducing the pH of the hydrolysate, and flowing the detoxified hydrolysate into a fermentation vessel containing a fermenting microorganism, thereby producing a fermentation product.

4. DETAILED DESCRIPTION

The present disclosure relates to methods for detoxifying a hydrolysate obtained from a biomass and methods of producing a fermentation product (e.g., ethanol) from the detoxified hydrolysate. Types of biomass that can be used in the present methods include but are not limited to those described in Section 4.1. Methods of hydrolyzing the biomass are described in Section 4.2. Typical compositions of hydrolysates prior to detoxification are described in Section 4.3. Methods of detoxifying the hydrolysates using magnesium bases are described in Section 4.4. Methods of fermenting the detoxified hydrolysate to produce fermentation products are described in Section 4.5 and methods of recovering the fermentation products are described in Section 4.6.

4.1. Biomass

The term "biomass," as used herein, refers to any composition comprising cellulose (optionally also hemicellulose and/or lignin).

Relevant types of biomasses which can be hydrolyzed or detoxified according to the methods of the disclosure can include biomasses obtained from agricultural crops such as, e.g., containing grains; corn stover, grass, bagasse, straw e.g. from rice, wheat, rye, oat, barley, rape, sorghum; tubers. e.g., beet and potato.

The biomass is preferably lignocellulosic. The lignocellulosic biomass is suitably from the grass family. The proper name is the family known as Poaceae or Gramineae in the class Liliopsida (the monocots) of the flowering plants. Plants of this family are usually called grasses, and include bamboo. There are about 600 genera and some 9,000-10,000 or more species of grasses (Kew Index of World Grass Species).

Poaceae includes the staple food grains and cereal crops grown around the world, lawn and forage grasses, and bamboo.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized leaf anatomy that particularly adapts them to hot climates and an atmosphere low in carbon dioxide. C3 grasses are referred to as "cool season grasses" while C4 plants are considered "warm season grasses".

Grasses may be either annual or perennial. Examples of annual cool season are wheat, rye, annual bluegrass (annual meadowgrass, *Poa annua* and oat). Examples of perennial cool season are orchardgrass (cocksfoot, *Dactylis glomerata*), fescue (*Festuca* spp.), Kentucky bluegrass and perennial ryegrass (*Lolium perenne*). Examples of annual warm season are corn, sudangrass and pearl millet. Examples of Perennial Warm Season are big bluestem, indiangrass, bermudagrass and switchgrass.

One classification of the grass family recognizes twelve subfamilies: These are 1) anomochlooideae, a small lineage of broad-leaved grasses that includes two genera (*Anomochloa, Streptochaeta*); 2) Pharoideae (aka Poaceae), a small lineage of grasses that includes three genera, including *Pharus* and *Leptaspis;* 3) Puelioideae a small lineage that includes the African genus *Puelia;* 4) Pooideae which includes wheat, barley, oats, brome-grass (*Bromus*) and reed-grasses (*Calamagrostis*); 5) Bambusoideae which includes bamboo; 6) Ehrhartoideae, which includes rice, and wild rice; 7) Arundinoideae, which includes the giant reed and common reed 8) Centothecoideae, a small subfamily of 11 genera that is sometimes included in Panicoideae; 9) Chloridoideae including the lovegrasses (*Eragrostis*, ca. 350 species, including teff), dropseed grasses (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae; 12) Danthoniodieae including pampas grass; with *Poa* which is a genus of about 500 species of grasses, native to the temperate regions of both hemisphere.

Agricultural grasses grown for their edible seeds are called cereals. Three common cereals are rice, wheat and maize (corn). Of all crops, 70% are grasses.

Therefore a preferred biomass is selected from the group consisting of the energy crops. In a further preferred embodiment, the energy crops are grasses. Preferred grasses include Napier Grass or Uganda Grass, such as *Pennisetum purpureum*; or, *Miscanthus*; such as *Miscanthus giganteus* and other varieties of the genus *miscanthus*, or Indian grass, such as *Sorghastrum nutans*; or, switchgrass, e.g., as *Panicum virgatum* or other varieties of the genus *Panicum*), giant reed (arundo donax), energy cane (*saccharum* spp.)., wood (including, e.g., wood chips, processing waste), paper, pulp, and recycled paper (including, e.g., newspaper, printer paper, and the like). In some embodiments the biomass is sugarcane, which refers to any species of tall perennial grasses of the genus *Saccharum*.

Other types of biomass include seeds, grains, tuber (e.g., potatoes and beets), plant waste or byproducts of food processing or industrial processing (e.g., stalks), corn and corn byproducts (including, e.g., corn husks, corn cobs, corn fiber, corn stover, and the like), wood and wood byproducts (including, e.g., processing waste, deciduous wood, coniferous wood, wood chips (e.g., deciduous or coniferous wood chips), sawdust (e.g., deciduous or coniferous sawdust)), paper and paper byproducts (e.g., pulp, mill waste, and recycled paper, including, e.g., newspaper, printer paper, and the like), soybean (e.g., rapeseed), barley, rye, oats, wheat, beets, sorghum sudan, milo, bulgur, rice, sugar cane bagasse, forest residue, agricultural residues, quinoa, wheat straw, milo stubble, citrus waste, urban green waste or residue, food manufacturing industry waste or residue, cereal manufacturing waste or residue, hay, straw, rice straw, grain cleanings, spent brewer's grain, rice hulls, *salix*, spruce, poplar, eucalyptus, *Brassica carinata* residue, *Antigonum leptopus*, sweetgum, *Sericea lespedeza*, Chinese tallow, hemp, rapeseed, *Sorghum bicolor*, soybeans and soybean products (soybean leaves, soybeans stems, soybean pods, and soybean residue), sunflowers and sunflower products (e.g., leaves, sunflower stems, seedless sunflower heads, sunflower hulls, and sunflower residue), Arundo, nut shells, deciduous leaves, cotton fiber, manure, coastal Bermuda grass, clover, Johnsongrass, flax, straw (e.g., barley straw, buckwheat straw, oat straw, millet straw, rye straw amaranth straw, spelt straw), amaranth and amaranth products (e.g., amaranth stems, amaranth leaves, and amaranth residue), alfalfa, and bamboo.

Yet further sources of biomass include hardwood and softwood. Examples of suitable softwood and hardwood trees include, but are not limited to, the following: pine trees, such as loblolly pine, jack pine, Caribbean pine, lodgepole pine, shortleaf pine, slash pine, Honduran pine, Masson's pine, Sumatran pine, western white pine, egg-cone pine, longleaf pine, patula pine, maritime pine, ponderosa pine, Monterey pine, red pine, eastern white pine, Scots pine, araucaria tress; fir trees, such as Douglas fir; and hemlock trees, plus hybrids of any of the foregoing. Additional examples include, but are not limited to, the following: eucalyptus trees, such as Dunn's white gum, Tasmanian blue gum, rose gum, Sydney blue gum, Timor white gum, and the *E. urograndis* hybrid; *populus* trees, such as eastern cottonwood, bigtooth aspen, quaking aspen, and black cottonwood; and other hardwood trees, such as red alder, Sweetgum, tulip tree, Oregon ash, green ash, and willow, plus hybrids of any of the foregoing.

4.2. Hydrolysis of Biomass

Any hydrolysis process can be used to prepare lignocellulosic hydrolysates, including acid hydrolysis and base hydrolysis. Acid hydrolysis is a cheap and fast method and can suitably be used. A concentrated acid hydrolysis is preferably operated at temperatures from 20° C. to 100° C., and an acid strength in the range of 10% to 45% (e.g., 10%, 10.5%, 11%, 11.5%, 12%, 12.5%, 13%, 13.5%, 14%, 14.5%, 15%, 15.5%, 16%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 37%, 37.5%, 38%, 38.5%, 39%, 39.5%, 40%, 41%, 41.5%, 42%, 42.5%, 43%, 43.5%, 44%, 44.5%, 45% or any range bounded by any two of the foregoing values). Dilute acid hydrolysis is a simpler process, but is optimal at higher temperatures (100° C. to 230° C.) and pressure. Different kinds of acids, with concentrations in the range of 0.001% to 10% (e.g., 0.001%, 0.01%, 0.05%, 0.1%, 0.15%, 0.2%, 0.25%, 0.3%, 0.35%, 0.4%, 0.5%, 0.6%, 0.7%, 0.8%, 0.9%, 1%, 2%, 3%, 4%, 5%, 5.5%, 6%, 6.5%, 7%, 7.5%, 8%, 8.5%, 9%, 9.5% or 10%, or any range bounded by any two of the foregoing values) are preferably used. Suitable acids including nitric acid, sulfurous acid, nitrous acid, phosphoric acid, acetic acid, hydrochloric acid and sulfuric acid can be used in the hydrolysis step. Preferably sulfuric acid is used.

Depending on the acid concentration, and the temperature and pressure under which the acid hydrolysis step is carried out, corrosion resistant equipment and/or pressure tolerant equipment may be needed.

The hydrolysis can be carried out for a time period ranging from 2 minutes to 10 hours (e.g., 2, 3, 4, 5, 6, 7, 8, 9, 10, 15, 20, 25, 26, 27, 28, 29, or 30 minutes, or 0.5, 0.75, 1, 1.5, 2, 2.5, 3, 3.5, 4, 4.5, 5, 5.5, 6, 6.5, 7, 7.5, 8, 8.5, 9, 9.5 or 10 hour, or range bounded by any two of the foregoing values), preferably 1 minute to 2 hours, 2 minutes to 15 minutes, 2 minutes to 2 hours, 15 minutes to 2 hours, 30 minutes to 2 hours, 10 minutes to 1.5 hours, or 1 hour to 5 hours.

The hydrolysis can also include, as an alternative (e.g., in the absence of) or in addition to (e.g., before or after) the acid treatment, a heat or pressure treatment or a combination of heat and pressure, e.g., treatment with steam, for about 0.5 hours to about 10 hours (e.g., 0.5, 1, 1.5, 2, 2.5, 3, 3.5, 4, 4.5, 5.5, 6, 6.5, 7, 7.5, 8, 8.5, 9, 9.5 or 10 hours, or any range bounded by any two of the foregoing values).

Variations of acid hydrolysis methods are known in the art and are encompassed by the methods of the present disclosure. For instance, the hydrolysis can be carried out by subjecting the biomass material to a two step process. The first (chemical) hydrolysis step is carried out in an aqueous medium at a temperature and a pressure chosen to effectuate primarily depolymerization of hemicellulose without achieving significant depolymerization of cellulose into glucose. This step yields slurry in which the liquid aqueous phase contains dissolved monosaccharides and soluble and insoluble oligomers of hemicellulose resulting from depolymerization of hemicellulose, and a solid phase containing cellulose and lignin. See, e.g., U.S. Pat. No. 5,536,325. In a preferred embodiment, sulfuric acid is utilized to affect the first hydrolysis step. After the sugars are separated from the first-stage hydrolysis process, the second hydrolysis step is run under harsher condition to hydrolyze the more resistant cellulose fractions.

In another embodiment, the hydrolysis method entails subjecting biomass material to a catalyst comprising a dilute solution of a strong acid and a metal salt in a reactor. The biomass material can, e.g., be a raw material or a dried material. This type of hydrolysis can lower the activation energy, or the temperature, of cellulose hydrolysis, ultimately allowing higher yields of fermentable sugars. See, e.g., U.S. Pat. Nos. 6,660,506; 6,423,145.

A further exemplary method involves processing a biomass material by one or more stages of dilute acid hydrolysis using about 0.4% to about 2% of an acid; followed by treating the unreacted solid lignocellulosic component of the acid hydrolyzed material with alkaline delignification. See, e.g., U.S. Pat. No. 6,409,841. Another exemplary hydrolysis method comprises prehydrolyzing biomass (e.g., lignocellulosic materials) in a prehydrolysis reactor; adding an acidic liquid to the solid lignocellulosic material to make a mixture; heating the mixture to reaction temperature; maintaining reaction temperature for a period of time sufficient to fractionate the lignocellulosic material into a solubilized portion containing at least about 20% of the lignin from the lignocellulosic material, and a solid fraction containing cellulose; separating the solubilized portion from the solid fraction, and removing the solubilized portion while at or near reaction temperature; and recovering the solubilized portion.

Hydrolysis can also comprise contacting a biomass material with stoichiometric amounts of sodium hydroxide and ammonium hydroxide at a very low concentration. See Teixeira et al., 1999, Appl. Biochem. and Biotech. 77-79:19-34. Hydrolysis can also comprise contacting a lignocellulose with a chemical (e.g., a base, such as sodium carbonate or potassium hydroxide) at a pH of about 9 to about 14 at moderate temperature, pressure, and pH. See PCT Publication WO 2004/081185.

Ammonia hydrolysis can also be used. Such a hydrolysis method comprises subjecting a biomass material to low ammonia concentration under conditions of high solids. See, e.g., U.S. Patent Publication No. 20070031918 and PCT publication WO 2006/110901.

Following hydrolysis, the hydrolyzed product comprises a mixture of acid or base, partially degraded biomass and fermentable sugars. Prior to further processing, the acid or base can be removed from the mixture by applying a vacuum. The mixture can also be neutralized prior to detoxification.

Prior to detoxification, the aqueous fraction comprising the solubilized sugars can be separated from insoluble particulates remaining in the mixture in a process referred to as solid/liquid separation. Methods for separating the soluble from the insoluble fractions include, but are not limited to, centrifugation (continuous, semi-continuous and batch), decantation and filtration. The hydrolyzed biomass solids can optionally be washed with an aqueous solvent (e.g., water) to remove adsorbed sugars.

The solids can be further processed prior to detoxification, for example dewatered. Dewatering can be suitably achieved with a screw press. The screw press is a machine that uses a large screw to pull a stream containing solids along a horizontal screen tube. Movement of the solids can be impeded by a weighted plate at the end of the tube. The pressure of this plate on the solid plug forces liquid out of the solids and through the holes in the sides of the screen tube and then along the effluent pipe. The screw will then push the remaining solids past the plate where they fall out onto a collection pad or conveyor belt below.

4.3. Hydrolysate Characteristics

Following hydrolysis and of the biomass the solid/liquid separation step, the lignocellulosic hydrolysate is subjected to detoxification. The relative amounts and concentrations of the individual compounds comprising the lignocellulosic hydrolysate solution prior to detoxification (i.e., starting lignocellulosic hydrolysate solution), including fermentable sugars, furan aldehydes, aliphatic acids and phenolics, are dependent on the particular lignocellulosic biomass and the hydrolysis method from which the hydrolysate was obtained.

In certain embodiments, the starting hydrolysate solution comprises (a) total fermentable sugars at a concentration ranging from 30 g/L to 160 g/L, from 40 g/L to 95 g/L, or from 50 g/L to 70 g/L; (b) furfural at a concentration ranging from 0.5 g/L to 10 g/L, from 2.5 g/L to 4 g/L, or from 1.5 g/L to 5 g/L; (c) 5-HMF at a concentration ranging from 0.1 g/L to 5 g/L, from 0.5 g/L to 2.5 g/L or from 1 g/L to 2 g/L (d) acetic acid at a concentration ranging from 2 g/L to 17 g/L or from 11 g/L to 16 g/L; (e) lactic acid at a concentration ranging from 0 g/L to 12 g/L or from 4 g/L to 10 g/L; (f) additional aliphatic acids (e.g., succinic acid, formic acid, butyric acid and levulinic acid) at concentrations ranging from 0 g/L to 2.5 g/L; and/or (g) phenolics at a concentration ranging from 0 g/L to 10 g/L, from 0.5 g/L to 5 g/L or from 1 g/L to 3 g/L. In these embodiments, the starting hydrolysate solution will be referred to herein as "1×".

In other embodiments, the starting hydrolysate can be more concentrated than 1×. For example, the starting hydrolysate solution can be 1.5-fold, 2-fold, 3-fold, 4-fold, 5-fold, 6-fold, 7-fold, 8-fold, 9-fold or 10-fold more concentrated than 1×. In these embodiments, the starting hydrolysate will be referred to as 1.5×, 2×, 3×, 4×, 5×, 6×, 7×, 8×, 9× and 10×, respectively.

In other embodiments, the starting hydrolysate can be less concentrated than 1×. For example, the starting hydrolysate solution can be 0.1-fold, 0.2-fold, 0.3-fold, 0.4-fold, 0.5-fold, 0.6-fold, 0.7-fold, 0.8-fold or 0.9-fold as concentrated as 1×. In these embodiments, the starting hydrolysate will be referred to as 0.1×, 0.2×, 0.3×, 0.4×, 0.5×, 0.6×, 0.7×, 0.8×, and 0.9, respectively.

The concentration of the hydrolysate solution can be adjusted prior to the detoxification process. Concentration of the hydrolysate solution can be particularly advantageous in the context of a continuous process (see FIG. 1 and Section 4.4). For example, a hydrolysate solution leaving a hydrolyzer following dilute acidic hydrolysis and solid/liquid separation can be concentrated prior to the addition of the magnesium base used for detoxification. In certain embodiments, the hydrolysate solution can be concentrated by 1.2-fold, 1.5-fold, 2-fold, 3-fold or 5-fold prior to detoxification. In specific embodiments, the starting hydrolysate can concentrated in a range bounded by any two of the foregoing embodiments, e.g., concentrated by 1-fold to 3-fold, 1.5-fold to 3-fold, 3-fold to 5-fold, etc.

Concentrating the hydrolysate solution prior to detoxification can result in increased selectivity for furan aldehyde elimination over sugar degradation. Without being bound by theory, it is believed that the rate of reaction is first order with respect to sugar degradation and second order with respect to furan aldehyde elimination. Accordingly, concentrating the hydrolysate solution results in increasing the rate of elimination of furan aldehydes relative to the rate of degradation of fermentable sugars.

The hydrolysate solution can be concentrated under reduced pressure and/or by applying heat. In one embodiment, the hydrolysate solution is concentrated in a multi-stage evaporation unit (see FIG. 1 and Example 1). Concentration of hydrolysate can also be performed by other technologies such as membrane filtration, carbon treatment and ion-exchange resin. Evaporation results in increased sugar concentration and can result in the removal of some amounts of furfural and acetate.

4.4. Detoxification of Hydrolysates with Magnesium Bases

The detoxification methods of the disclosure generally entail mixing a lignocellulosic hydrolysate with a magnesium base (e.g., magnesium hydroxide, magnesium carbonate or magnesium oxide) for a period of time and under conditions that result in the production of a detoxified lignocellulosic hydrolysate. The detoxification methods are highly selective towards elimination of furan aldehydes. As used herein, the phrase "highly selective towards elimination of furan aldehydes" refers to the observation that furan aldehydes react with magnesium bases at higher rates than fermentable sugars react with magnesium bases. As a result, the detoxified hydrolysates produced in accordance with the present disclosure have a larger percentage of fermentable sugars and a lower percentage of furan aldehydes relative to the starting hydrolysate. The detoxified hydrolysates can then be fermented by a suitable fermenting microorganism to produce a fermentation product such as ethanol.

The detoxification methods typically comprise mixing a starting lignocellulosic hydrolysate solution with a magnesium base for a period of time and under conditions that result in the production of a detoxified hydrolysate solution. The amount of time suitable to perform the detoxification process depends on a number of factors, including the chemical composition of the hydrolysate, the concentration of the hydrolysate solution, the reaction temperature, the pH of the hydrolysate solution, the total amount of magnesium base added, the stirring rate, and the type of reactor being used. The detoxification process is typically carried out for a period of time ranging from 15 minutes to 80 hours, and more typically between 1 hour and 40 hours. In specific embodiments, the detoxification process is carried out for a period of time ranging from 1 hour to 30 hours, from 1.5 hours to 20 hours, from 2 hours to 12 hours, from 3 hours to 9 hours, from 4 hours to 10 hours, or from 6 hours to 9 hours. This process is applicable for batch and continuous vessel treatments.

The hydrolysate detoxification process is typically carried out at a temperature of 90° C. or less, for example at a temperature of 30° C., 35° C., 40° C., 45° C., 50° C., 55° C., 60° C., 70° C., 75° C., 80° C. or 85° C. In specific embodiments, the temperature is in the range bounded by any of the two foregoing embodiments, such as, but not limited to, a temperature ranging from 40° C. to 70° C., from 40° C. to 60° C., from 40° C. to 55° C., from 45° C. to 55° C., from 45° C. to 50° C., from 50° C. to 55° C., or from 40° C. to 50° C. In particular embodiments, the temperature of the hydrolysate solution is in the range from 40° C. to 60° C. In this range, high selectivity for furan aldehyde elimination is achieved while commercially feasible rates of the detoxification reactions are observed.

The hydrolysate detoxification process is typically carried out at a pH ranging from 6.2 to 9.5, for example at a pH of 6.5, 7, 7.5, 8, 8.5, 9.0 or 9.5. In specific embodiments, the pH is in the range bounded by any of the two foregoing values, such as, but not limited to, a pH ranging from 6.5 to 8, from 6.5 to 7.5, from 7 to 8, or from 7 to 7.5. It will be understood that the pH of the hydrolysate solution depends on the concentration of the magnesium base and the temperature of the solution. In embodiments where hydrolysate detoxification is carried out using magnesium hydroxide, the solubility of the magnesium hydroxide decreases with increasing temperature. Therefore, for a given amount of magnesium hydroxide added to the hydrolysate solution, the equilibrium pH decreases as the temperature is increased, all other variables being constant (see, e.g., Table 3). The pH of the solution can decrease slightly as the detoxification process progresses owing to the consumption of hydroxide in reaction with sugars and furans. Additional magnesium hydroxide can be added to the hydrolysate solution to adjust the pH during the course of the reaction.

The total amount of magnesium base added to hydrolysate solution 1× can range from 2 grams per 1 kilogram hydrolysate (2 g/1 kg hydrolysate) to 200 grams per 1 kilogram hydrolysate (200 g/1 kg hydrolysate). For instance, the total amount of magnesium base added to the hydrolysate solution can be 40 g/1 kg hydrolysate, 80 g/1 kg hydrolysate, 100 g/1 kg hydrolysate, 120 g/1 kg hydrolysate, 140 g/1 kg hydrolysate, or 160 g/1 kg hydrolysate. The magnesium base can be added to the hydrolysate solution in a single step, in multiple portions or continuously throughout the course of the detoxification process. In specific embodiments, the total amount of magnesium base added to the hydrolysate solution is in the range bounded by any of the two foregoing embodiments, such as, but not limited to, from 40 g/1 kg hydrolysate to 160 g/1 kg hydrolysate, from 40 g/1 kg hydrolysate to 120 g/1 kg hydrolysate, from 80 g/1 kg hydrolysate to 160 g/1 kg hydrolysate, from 80 g/1 kg hydrolysate to 140 g/1 kg hydrolysate, or from 140 g/1 kg hydrolysate to 160 g/1 kg hydrolysate. For more concentrated hydrolysate solutions (e.g., 4×), the amount of magnesium base sufficient to raise the pH to the desired level would be increased relative to hydrolysate solution 1×. For less concentrated hydrolysate solutions (e.g., 0.5×), the amount of magnesium base sufficient to raise the pH to the desired level would be decreased relative to hydrolysate solution 1×.

The hydrolysate detoxification process can be performed in any suitable vessel, such as a batch reactor or a continuous reactor (e.g., a continuous stirred tank reactor (CSTR) or a plug flow reactor (PFR). A continuous reactor allows for continuous addition and removal of input materials (e.g., hydrolysate, magnesium base slurry) as the detoxification reaction progresses. The suitable vessel can be equipped with a means, such as impellers, for agitating the hydrolysate solution. Reactor design is discussed in Lin, K.-H., and Van Ness, H. C. (in Perry, R. H. and Chilton, C. H. (eds), Chemical Engineer's Handbook, 5th Edition (1973) Chapter 4, McGraw-Hill, NY.

The detoxification processes can be carried out in a batch mode. The methods typically involve combining the hydrolysate solution and the magnesium base (or magnesium base slurry) in the reactor. The hydrolysate solution and the magnesium base can be fed to the reactor together or separately. Any type of reactor can be used for batch mode detoxification, which simply involves adding material, carrying out the detoxification process at specified conditions (e.g. temperature, dosage and time) and removing the detoxified hydrolysate from the reactor.

Alternatively, the detoxification processes can be carried out in a continuous mode. The continuous processes of the disclosure advantageously reduces the need to stop and clean reactors and accordingly can be carried out in continuous mode, e.g., for periods of several days or longer (e.g., a week or more) to support an overall continuous process. The methods typically entail continuously feeding a hydrolysate solution and magnesium base slurry to a reactor. The hydrolysate and the magnesium base slurry can be fed together or separately. The resultant mixture has a particular retention or residence time in the reactor. The residence time is determined by the time to achieve the desired level of detoxification following the addition of the hydrolysate and the base to the reactor. Following the detoxification process, the detoxified hydrolysate exits the reactor and additional components (e.g., hydrolysate and base slurry) are added to the reactor. Multiple such reactors can be connected in series to support further pH adjustment during an extended retention time and/or to adjust temperature during an extended retention time For detoxification in continuous mode, any reactor can be used that allows equal input and output rates, e.g., a continuous stirred tank reactor or plug flow reactor, so that a steady state is achieved in the reactor and the fill level of the reactor remains constant.

The detoxification processes of the disclosure can be carried out in semicontinuous mode. Semicontinuous reactors, which have unequal input and output streams that eventually require the system to be reset to the starting condition, can be used.

Figure 1:
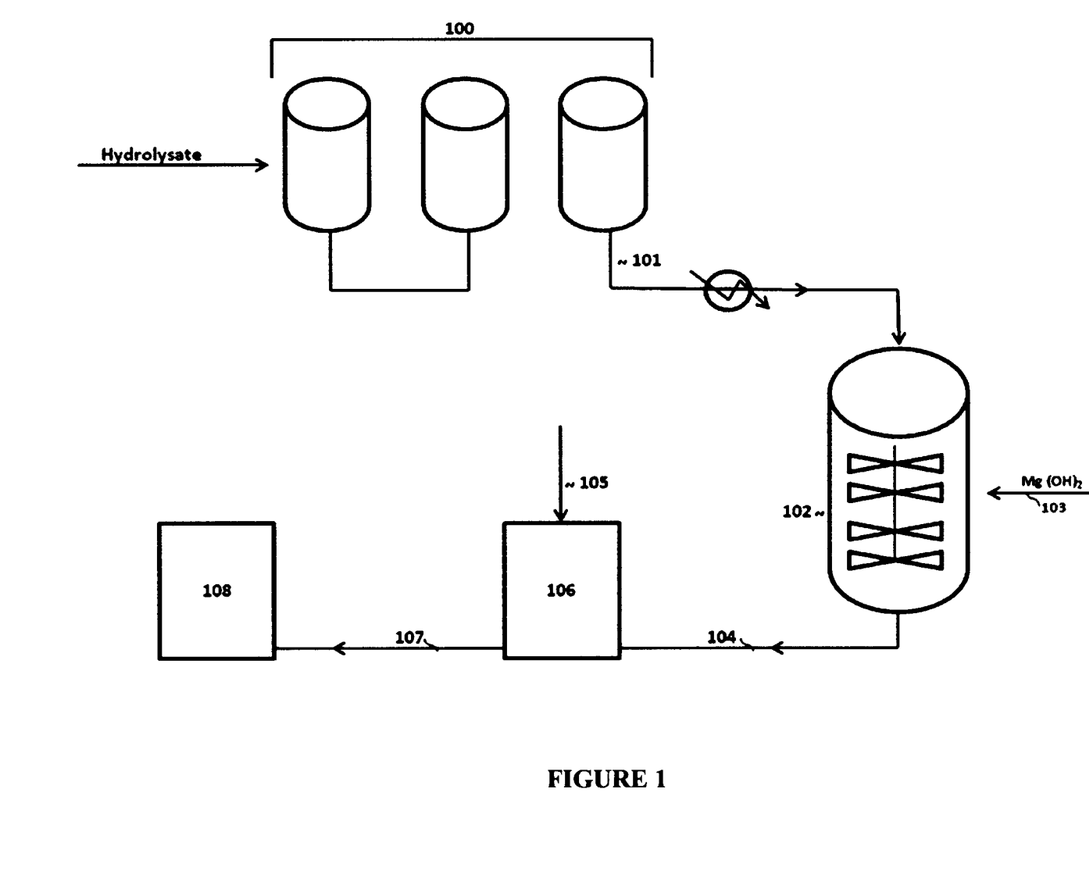
FIG. 1: Schematic of a flow diagram of an exemplary continuous process of the present disclosure.

The present disclosure provides methods of continuously detoxifying a biomass obtained from a lignocellulosic biomass. As depicted in FIG. 1, steps of the continuous detoxification process include flowing a first continuous stream of a hydrolysate into a continuous reactor, flowing a second continuous stream of a solution of a magnesium base into the continuous reactor, mixing the hydrolysate with the magnesium base in the continuous reactor for a period of time sufficient to reduce the quantity of toxins in the hydrolysate, and flowing the hydrolysate out of the continuous reactor.

The methods of the disclosure can include further steps in addition to detoxification, such as one or more steps depicted in FIG. 1 that are upstream or downstream of the detoxification step. In FIG. 1, only steps that are downstream of biomass hydrolysis are depicted. Following hydrolysis of the biomass and solid/liquid separation, the hydrolysate is concentrated in a multi-stage evaporation unit 100. The hydrolysate leaves the multi-stage evaporation unit 100 through line 101 and enters continuous stirred tank reactor 102. The hydrolysate can be heated prior to entering continuous stirred tank reactor 102. Magnesium hydroxide is supplied continuously to the continuous stirred tank reactor through line 103. After the detoxification in continuous stirred tank reactor 102 is complete, the detoxified hydrolysate is passed into line 104, where it is met with a stream of acid (e.g., sulfuric acid or phosphoric acid) from line 105. The mixture of detoxified hydrolysate is passed into mixer 106. The neutralized detoxified hydrolysate exits mixer 106 through line 107 and flows into fermentation vessel 108.

Adequate mixing of the hydrolysate solution following addition of the magnesium base can improve the rate of dissolution of the base and ensure that the pH remains substantially homogeneous throughout the solution. For instance, ideal mixing will avoid the formation of local pockets of higher pH, which can result in lower selectivity for furan elimination. Mixing speeds of between 100 revolutions per minute (rpm) and 1500 rpm can be used to ensure sufficient mixing of the hydrolysate solution. For instance, mixing speeds of 100 rpm, 200 rpm, 400 rpm, 800 rpm and 1500 rpm can be used. In specific embodiments, mixing is carried out at speeds bounded by any two of the foregoing mixing speeds, such as, but not limited to from 100 rpm to 200 rpm, from 100 rpm to 400 rpm, from 200 rpm to 400 rpm, from 400 rpm to 800 rpm or from 800 rpm to 1,500 rpm. In other embodiments, intermittent mixing regimes can be used where the rate of mixing is varied as the detoxification process progresses. Mixing of the hydrolysate solution can be accomplished using any mixer known in the art, such as a high-shear mixer, paddle mixer, magnetic stirrer or shaker, vortex, agitation with beads, and overhead stirring.

The detoxification methods of the present disclosure provide detoxified hydrolysates in which a substantial portion of the furan aldehydes have been removed relative to the starting hydrolysate. At the same time, the detoxification results in minimal loss of fermentable sugars. Therefore, the detoxification reactions are highly selective towards elimination of furan aldehydes. In particular embodiments, methods disclosed herein provide a detoxified hydrolysate with at least 70%, at least 80%, at least 85%, at least 90%, at least 95% or at least 99% of the fermentable sugars present in the starting hydrolysate and no greater than 50%, no greater than 40%, no greater than 30%, or no greater than 20% of the furan aldehydes present in the staring hydrolysate solution.

In particular embodiments, detoxification methods of the present disclosure provide a detoxified hydrolysate with (a) at least 90% of the total fermentable sugars present in the starting hydrolysate and no greater than 50% of the furan aldehyde present in the starting hydrolysate; (b) at least 90% of the total fermentable sugars present in the starting hydrolysate and no greater than 40% of the furan aldehydes present in the starting hydrolysate; (c) at least 90% of the total fermentable sugars present in the starting hydrolysate and no greater than 30% of the furan aldehydes present in the starting hydrolysate; (d) at least 90% of the total fermentable sugars present in the starting hydrolysate and no greater than 20% of the furan aldehydes present in the starting hydrolysate; (e) at least 80% of the total fermentable sugars present in the starting hydrolysate and no greater than 50% of the furan aldehydes present in the starting hydrolysate; (f) at least 80% of the total fermentable sugars present in the starting hydrolysate and no greater than 40% of the furan aldehydes present in the starting hydrolysate; (g) at least 80% of the total fermentable sugars present in the starting hydrolysate and no greater than 30% of the furan aldehydes present in the starting hydrolysate; (h) at least 80% of the total fermentable sugars present in the starting hydrolysate and no greater than 20% of the furan aldehydes present in the starting hydrolysate.

In particular advantageous embodiments, the magnesium base used for detoxification is magnesium hydroxide. An advantage of magnesium hydroxide is that it effectively buffers the hydrolysate solution as the detoxification process proceeds. Owing to the limited solubility of magnesium hydroxide, the solid magnesium hydroxide only dissociates further in a neutral or alkaline system after the hydroxide ions react with the other components (e.g., furan aldehydes) comprising the hydrolysate. Furthermore, due to the common ion effect, as hydroxide is consumed in reaction with either furan aldehydes or sugars, the accumulation of soluble magnesium ion (which does not react and is present as an observer ion) would prevent further solubilization of magnesium hydroxide and thus creates a limit on further pH increase. Therefore, the pH of the solution remains within a narrow range throughout the course of the detoxification process.

Without being bound by theory, it is believed that the high selectivity towards elimination of furan aldehydes observed using methods of the present disclosure stems in part from the tight pH control achieved with magnesium hydroxide or magnesium carbonate as a detoxification base. Titration studies indicate that magnesium hydroxide has a low solubility in hydrolysate solutions, particularly at a pH in the range of 6 to 8, where the detoxification process is generally performed (see FIG. 3 and Example 6). Therefore, the quantity of hydroxide ion in the hydrolysate solution available to react with the components of the hydrolysate (e.g., total fermentable sugars and furan aldehydes) is limited. Kinetic studies (see Example 7) suggest that the activation energy for furfural destruction is lower than that for sugar degradation. Accordingly, the large majority of the hydroxide present in solution is directed towards reactions with the furan aldehydes rather than the total fermentable sugars.

After the detoxification process is complete, the pH of the detoxified hydrolysate solution can be lowered by adding a suitable acid (e.g., sulfuric acid or phosphoric acid) (see FIG. 1). The pH can be adjusted to a level that is suitable for a fermenting microorganism. Generally, the pH is adjusted to a value between 3.5 and 8, and more typically between a value of 4 and 7. After the pH is adjusted to the desired level, the detoxified hydrolysate can be transferred to a fermentation vessel.

4.5. Fermentation of Detoxified Hydrolysates

The fermentation of sugars to fermentation products can be carried out by one or more appropriate fermenting microorganisms in single or multistep fermentations. Fermenting microorganisms can be wild type microorganisms or recombinant microorganisms, and include *Escherichia, Zymomonas, Saccharomyces, Candida, Pichia, Streptomyces, Bacillus, Lactobacillus*, and *Clostridium*. Particularly suitable species of fermenting microorganisms include *Escherichia coli, Zymomonas mobilis, Bacillus stearothermophilus, Saccharomyces cerevisiae, Clostridia thermocellum, Thermoanaerobacterium saccharolyticum*, and *Pichia stipitis*. Geneti cally modified strains of E. coli or Zymomonas mobilis can be used for ethanol production (see, e.g., Underwood et al., 2002, Appl. Environ. Microbiol. 68:6263-6272 and US 2003/0162271 A1).

The fermentation can be carried out in a minimal media with or without additional nutrients such as vitamins and corn steep liquor (CSL). The fermentation can be carried out in any suitable fermentation vessel known in the art. For instance, fermentation can be carried out in an Erlenmeyer flask, Fleaker, DasGip fedbatch-pro (DasGip technology), 2 L BioFlo fermenter or 10 L fermenter (B. Braun Biotech) (see Example 7). The fermentation process can be performed as a batch, fed-batch or as a continuous process. The starting pH of the fermentation broth ranges from a value of 3.5 to a value of 8, and more typically from a value of 4 to a value of 7. The fermentation is generally carried out at a temperature between 20° C. and 40° C., and more typically between 25° C. and 35° C. In particular embodiments, the fermentation is carried out for a period of time between 5 to 90 hours, 10 to 50 hours, or from 20 to 40 hours.

4.6. Recovery of Fermentation Products

Fermentation products can be recovered using various methods known in the art. Products can be separated from other fermentation components by centrifugation, filtration, microfiltration, and nanofiltration. Products can be extracted by ion exchange, solvent extraction, or electrodialysis. Flocculating agents can be used to aid in product separation. As a specific example, bioproduced ethanol can be isolated from the fermentation medium using methods known in the art for ABE fermentations (see for example, Dune, 1998, Appl. Microbiol. Biotechnol. 49:639-648; Groot et al., 1992, Process. Biochem. 27:61-75; and references therein). For example, solids can be removed from the fermentation medium by centrifugation, filtration, decantation, or the like.

After fermentation, the fermentation product, e.g., ethanol, can be separated from the fermentation broth by any of the many conventional techniques known to separate ethanol from aqueous solutions. These methods include evaporation, distillation, azeotropic distillation, solvent extraction, liquid-liquid extraction, membrane separation, membrane evaporation, adsorption, gas stripping, pervaporation, and the like.

5. EXAMPLES

5.1. Example 1

Hydrolysis of Lignocellulosic Biomasses

A lignocellulosic biomass (e.g., energy cane or sugar cane) was harvested and sized using a forage chopper, inoculated with a preparation of Lactobacillus bacteria and stored in agricultural bags until use. Prior to dilute acid hydrolysis, the lignocellulosic biomass was removed from bags and washed with process water to remove organic acids and then dewatered with a screw press. The biomass was then conveyed to a pressurized reaction chamber (i.e., hydrolyzer) along with water and sulfuric acid (0.2% to 3%). The liquid/solid ratio of the slurry was minimized to maximize the dissolved sugar concentration in the hydrolysate following hydrolysis. The retention time in the hydrolyzer and the temperature of the hydrolyzer was dependent on parameters of the biomass (e.g., moisture and glucan levels). In general, the temperature of the hydrolyzer ranged from 120° C. to 180° C. and the retention time ranged from 3 minutes to 2 hours.

Following dilute-acid hydrolysis, the resultant hydrolyzer slurry contained solubilized sugars as well as residual insoluble fiber. The slurry was explosively decompressed and blown into a cyclone unit to depressurize the slurry. The material was reslurried with wash water and screw presses were used for dewatering the slurry in order to wring out soluble sugars and toxins. Three screw press steps with countercurrent washing were used to dewater and wash the cake of inhibitors. Countercurrent washing is defined as wash water flowing in the opposite direction to the cake flow. The high-percent solids slurry was diluted to a low percent solids slurry (<10% solids) and pumped to a screw press. This dilution was performed with a fraction of recycled liquids delivered by counter-current exchange from later screw presses (defined as "pressate") as the system achieved steady-state. Clean water was added at the final screw press step along with the pressate to make the cake pumpable. The primary liquid/solid separation step was repeated with two more screw presses to remove toxins from the cake. The resulting high percent solids cake was carried forward for simultaneous saccharification and fermentation and the pressate from the first step was collected for detoxification work.

The concentrations of the individual compounds (e.g., sugars, furans and aliphatic acids) in the starting hydrolysate from several biomass sources following dilute acid hydrolysis and solid/liquid separation are shown in Table 1.

TABLE 1

| | | | | | total | | | succinic | lactic | formic | acetic | butyric | levulinic |
| | | glucose | xylose | Arabinose | sugar | 5-HMF | Furfural | acid | acid | acid | acid | acid | acid |
| Name | Source | (g/L) | (g/L) | (g/L) | (g/L) | (g/L) | (g/L) | (g/L) | (g/L) | (g/L) | (g/L) | (g/L) | (g/L) |
| --- | --- | --- | --- | --- | --- | --- | --- | --- | --- | --- | --- | --- | --- |
| DP 110105 | Sugar Cane | 22.74 | 67.05 | 6.83 | 96.61 | 1.04 | 3.13 | 0.00 | 2.04 | 1.37 | 15.55 | 0.00 | 1.03 |
| DP 100309 | Sorghum | 14.4 | 42.55 | 7.00 | 63.95 | 0.36 | 2.05 | 0.22 | 10.92 | 0.53 | 11.53 | 0 | ND |
| DP 100511 | Energy Cane | 11.01 | 46.6 | 6.25 | 63.86 | 0.33 | 1.7 | 0.00 | 6.85 | 0.43 | 9.83 | 0 | 0.49 |
| DP 100513-1 | Energy Cane | 10.75 | 57.27 | 8.55 | 76.56 | 0.36 | 2.73 | 0.33 | 10.06 | 0.50 | 11.59 | 0.00 | 0.61 |
| DP 100513-2 | Energy Cane | 15.1 | 54.2 | 7.95 | 77.25 | 0.42 | 2.97 | 0.064 | 12.00 | 0.66 | 14.34 | 0.00 | 0.61 |

Composition of Starting Hydrolysates

5.2. Example 2

Detoxification of Hydrolysates with Magnesium Hydroxide—Batch Reactor

5.2.1. Materials and Methods
5.2.1.1. Sorghum Hydrolysate DP 100309

Hydrolysate DP 100309 was placed in a 1 L three necked round bottom flask equipped with stir bars. The round bottom flask was placed in oil bath and heated to 70° C. While the hydrolysate solution was warming, target amounts of magnesium hydroxide slurry (i.e., supersaturated solution of magnesium hydroxide in water) were weighed. The total quantity of magnesium hydroxide added to the hydrolysate was determined from the titration of the hydrolysate solution with sodium hydroxide (see FIG. 3 and Example 6). Also, see Martinez et al., 2001, Biotechnol. Prog. 17(2):287-293. After the hydrolysate solution was heated to the desired temperature, the magnesium hydroxide slurry was added rapidly to the hydrolysate solution at a dosage of 22.86 g/Kg hydrolysate at 70° C. The solution was stirred vigorously with a magnetic stirrer for 3 hours. The progress of the detoxification process was monitored over time. Samples from the hydrolysate solution at various time points were taken and quenched with a stop solution (50 mM $H_2SO_4$) on ice (approximately 1.3 ml of each time point sample was immediately added to 11.7 ml of ice cold stop solution (50 mM $H_2SO_4$, 10× fold dilution) to quench any further reaction from occurring on the time scale of further chemical analysis). After the detoxification process was complete, the detoxified hydrolysate was then cooled to the fermentation temperature, and pH was adjusted to fermentation pH by adding 4M $H_2SO_4$.

Following acidification of the detoxified hydrolysate solution, the concentrations of the individual compounds in the hydrolysate were measured. Sugars were separated and quantified by HPLC. A Shodex SP0810 size exclusion and ligand exchange column was used with an Agilent 1200 series refractive index detector (RID). An isocratic method was run using HPLC grade water as a mobile phase which provides enough resolution to generate a chromatogram from which the different sugar concentrations can be calculated, including xylose, arabinose, glucose, cellobiose, galactose, mannose, and other sugars.

Furfural and 5-HMF concentrations were also analyzed by HPLC using an Alltech Platinum C18 column and the same Agilent RID. Samples are diluted into a water/acetonitrile mixture and transferred into vials or well plate. These samples are identified and quantified by retention times and peak area against standard curves against known concentrations of various analytes.

5.2.1.2. Energy Cane Hydrolysate DP 100511

Hydrolysate DP 100511 was placed in a 1 L three necked round bottom flask equipped with stir bars. The round bottom flask was placed in oil bath and heated to 70° C. While the hydrolysate solution was warming, target amounts of magnesium hydroxide slurry were weighed. After the hydrolysate solution was heated to the desired temperature, the magnesium hydroxide slurry was added rapidly to the hydrolysate solution at a dosage of 16.53 g/Kg hydrolysate at 70° C. The solution was stirred vigorously with a magnetic stirrer for 3 hours. The progress of the detoxification process was monitored over time. Samples from the hydrolysate solution at various time points were taken and quenched with a stop solution (50 mM $H_2SO_4$) on ice (approximately 1.3 ml of each time point sample was immediately added to 11.7 ml of ice cold stop solution (50 mM $H_2SO_4$, 10× fold dilution) to quench any further reaction from occurring on the time scale of further chemical analysis). After the detoxification process was complete, the detoxified hydrolysate was then cooled to the fermentation temperature, and pH was adjusted to fermentation pH by adding 4M $H_2SO_4$.

Following acidification of the detoxified hydrolysate solution, the concentrations of the individual compounds in the hydrolysate were measured as described in Section 5.2.1.1.

5.2.1.3 Energy Cane Hydrolysate DP 100513-1

Hydrolysate DP 100513-1 was placed in a 1 L three necked round bottom flask equipped with stir bars. The round bottom flask was placed in oil bath and heated to 70° C. While the hydrolysate solution was warming, target amounts of magnesium hydroxide slurry were weighed. After the hydrolysate solution was heated to the desired temperature, the magnesium hydroxide slurry was added rapidly to the hydrolysate solution at a dosage of 22.59 g/Kg hydrolysate at 70° C. The solution was stirred vigorously with a magnetic stirrer for 10 hours. The progress of the detoxification process was monitored over time. Samples from the hydrolysate solution at various time points were taken and quenched with a stop solution (50 mM $H_2SO_4$) on ice (approximately 1.3 ml of each time point sample was immediately added to 11.7 ml of ice cold stop solution (50 mM $H_2SO_4$, 10× fold dilution) to quench any further reaction from occurring on the time scale of further chemical analysis). After the detoxification process was complete, the detoxified hydrolysate was then cooled to the fermentation temperature, and pH was adjusted to fermentation pH by adding 4M $H_2SO_4$.

Following acidification of the detoxified hydrolysate solution, the concentrations of the individual compounds in the hydrolysate were measured as described in Section 5.2.1.1.

5.2.2. Results
5.2.2.1. Selectivity of Biomass Detoxification of Various Hydrolysates Results for detoxification of lignocellulosic hydrolysates obtained from sorghum (DP 100309) and energy cane (DP 100511 and DP 100513-1) carried out at either 50° C. or 70° C. are shown in Table 2. The results shown in Table 2 indicate that detoxification reactions have far greater selectivity for furan aldehyde removal than for sugar loss. The percentage of sugar loss at the indicated time point was 7% or less, while the percentage of furan removal was 29.5% or greater. Hydrolysate solutions with a higher initial concentration of furan aldehydes were mixed with the magnesium hydroxide for longer times to achieve the desired level of furan aldehyde elimination under a standard set of conditions. For example, hydrolysate DP 100511, obtained from energy cane, which had a starting concentration of 1.7 g/L furfural, was detoxified for 3 hours at 70° C. to achieve the desired level of furfural elimination. On the other hand, hydrolysate DP 100513-1, also obtained from energy cane, which had a starting concentration of 2.73 g/L furfural, was detoxified for 10 hours at 70° C. to achieve the desired level of furfural elimination.

The selectivity of the detoxification process is also dependent on temperature. For instance, starting with hydrolysate DP 100513-1, obtained from energy cane, negligible amounts of sugars were lost after 9 hours when the detoxification process was run at a temperature of 50° C. At 70° C., 5% of the sugars were lost when the same hydrolysate was detoxified for 9 hours, all other conditions being the same. However, the percentage of furfural removal for the detoxification process run at 70° C. for 9 hours was more than twice that of the detoxification at 50° C. for nine hours. Hence, at lower temperatures, longer reaction times provide acceptable levels of furan elimination.

TABLE 2

Selectivity of Biomass Detoxification of Different Hydrolysates Using Magnesium Hydroxide as a Base

| Name | Source | Grams of magnesium hydroxide/Kg of Hydrolysate | Initial Sugar concentration (g/L) | Initial Furfural concentration (g/L) | Reaction temp (° C.) | Reaction Time (h) | Initial pH | pH following base addition | Selectivity % sugar loss | % furfural removal | Final furfural (g/L) |
|---|---|---|---|---|---|---|---|---|---|---|---|
| DP 100309 | sorghum | 22.86 | 64 | 2.05 | 70 | 3 | 1.23 | 6.2 | 7 | 60.8 | 0.8 |
| DP 100511 | energy cane | 16.53 | 64 | 1.7 | 70 | 3 | 1.48 | 6.1 | 4 | 40.9 | 1.04 |
| DP 100513-1 | energy cane | 22.59 | 76.6 | 2.73 | 70 | 10 | 1.41 | 5.9 | 6.4 | 64.6 | 1.1 |
| DP 100513-1 | energy cane | 22.59 | 76.6 | 2.73 | 50 | 9 | 1.2 | 5.7 | 0 | 29.5 | 1.89 |
| DP 100513-1 | energy cane | 22.59 | 76.6 | 2.73 | 70 | 9 | 1.28 | 5.6 | 5 | 63.1 | 0.99 |

Figure 2A:
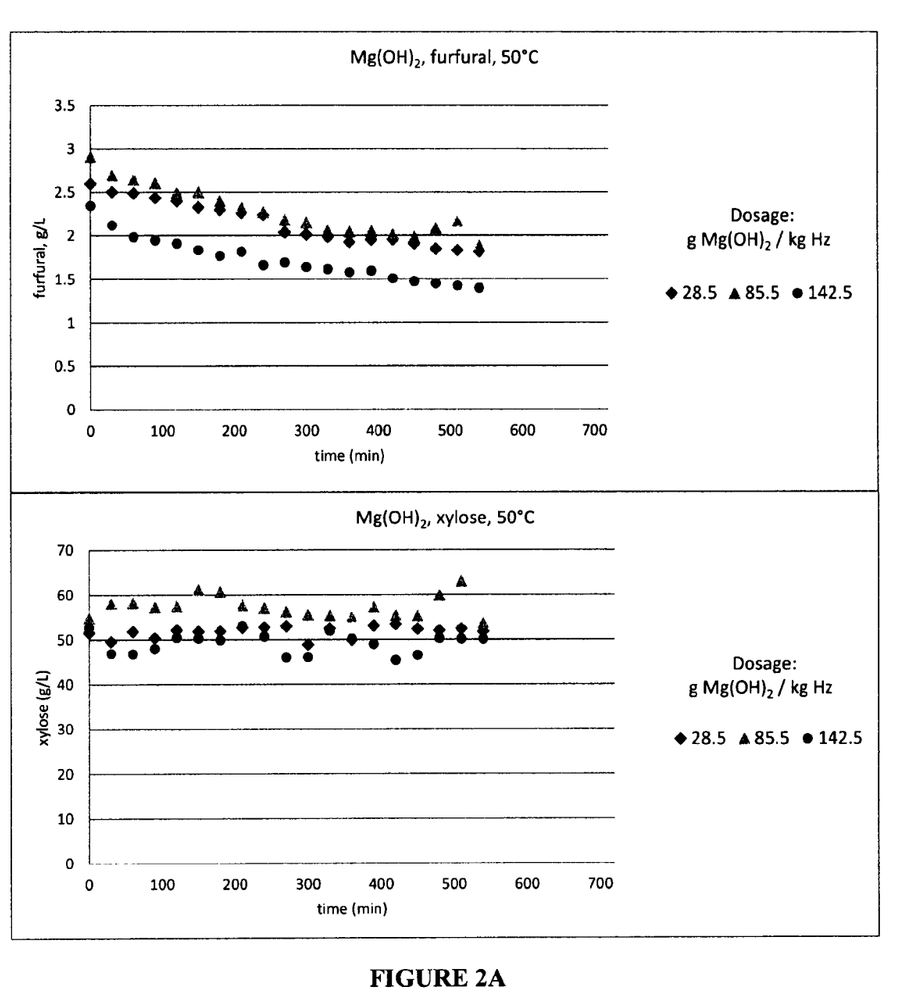
FIGS. 2A-2C: Graphs depicting the amount of xylose and furfural elimination at different time points for detoxification reactions using various dosages (i.e., 28.5 g magnesium hydroxide/1 kg hydrolysate, 85.5 g magnesium hydroxide/1 kg hydrolysate, and 142.5 g magnesium hydroxide/1 kg hydrolysate) performed at 50° C., 70° C. and 90° C., respectively.
Figure 2B:
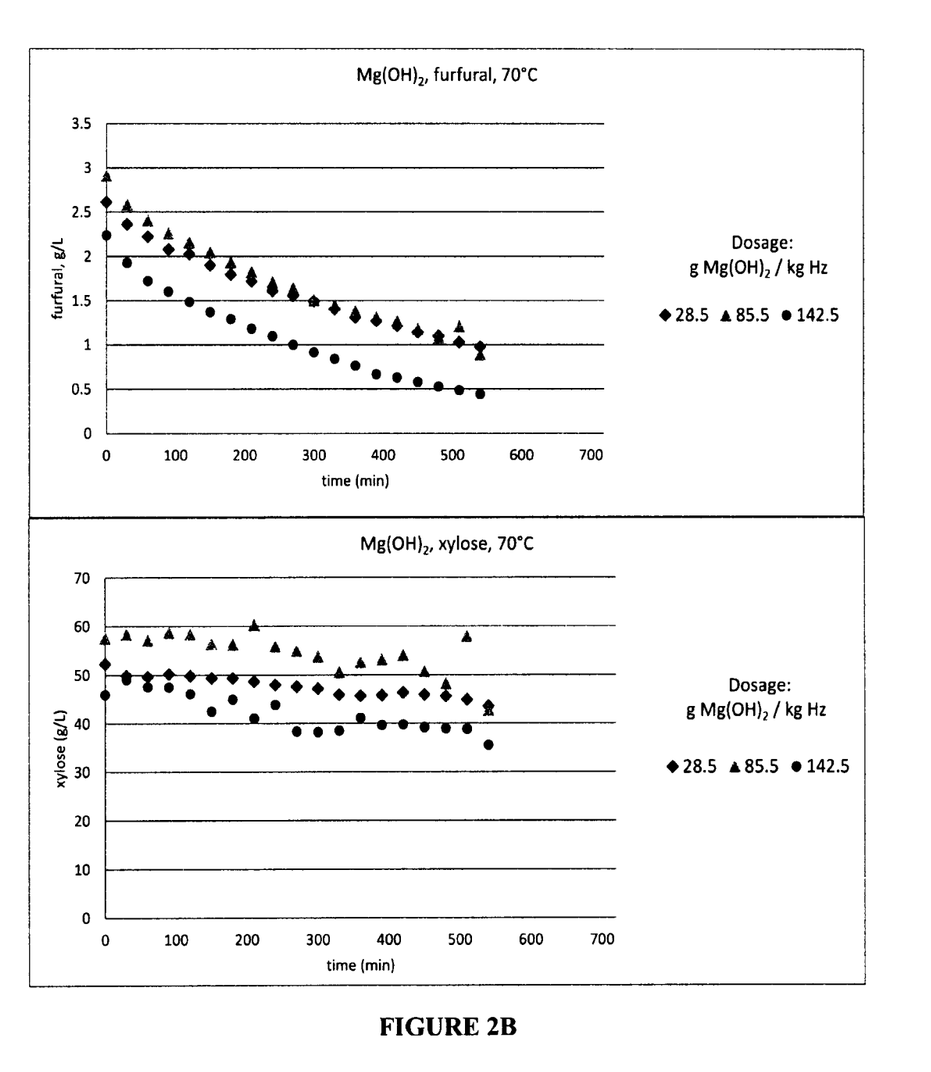
Figure 2C:
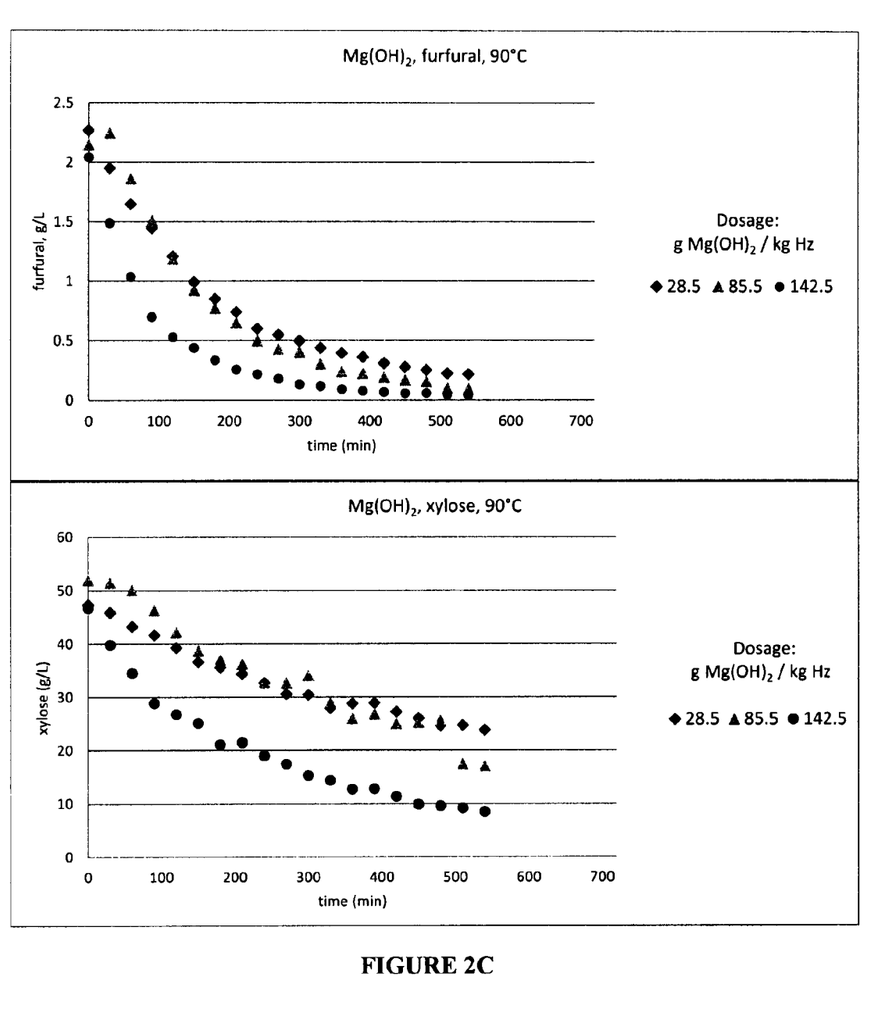

5.2.2.2. Detoxification of Hydrolysate Obtained from Energy Cane at Varying Concentrations of Base and at Various Temperatures A hydrolysate obtained from energy cane (DP 100513-1) was subjected to the detoxification procedure described above using varying amounts of magnesium hydroxide at temperatures of 50° C., 70° C. and 90° C. The concentrations of the individual compounds of hydrolysate DP 100513-1 are shown in Table 1. FIGS. 2A-2C provide graphs depicting the amount of xylose and furfural elimination at various time points for detoxification reactions using various dosages (i.e., 28.5 g magnesium hydroxide/1 kg hydrolysate, 85.5 g magnesium hydroxide/1 kg hydrolysate, and 142.5 g magnesium hydroxide/1 kg hydrolysate) performed at 50° C., 70° C. and 90° C., respectively. At 50° C. (FIG. 2A), the selectivity for furfural elimination is high, irrespective of the concentration of magnesium hydroxide used. The rate of furfural elimination increases with increasing dosages of magnesium hydroxide. At a temperature of 70° C. (FIG. 2B), the selectivity for furfural elimination is still significant, albeit less than the selectivity at 50° C. The rate of furfural elimination is slightly faster at 70° C. than at 50° C. At 90° C. (FIG. 2C), the selectivity for furfural elimination is reduced relative to that of detoxifications run at 50° C. and 70° C. and more sugars are consumed in the process than detoxifications run at lower temperatures. The rate of furfural elimination is significantly greater at 90° C. than at 50° C. or at 70° C.

5.3. Example 3

Detoxification of Hydrolysates—Series of CSTRs

The detoxification process is carried out using a series of continuously stirred tank reactors (CSTRs). The hydrolysate solution is heated to the target temperature with heating mantles and/or recirculating water bath and delivered by peristaltic pump to the first of a series of stirred reactors (1, 2, or 4 L sizes) connected in series to which magnesium hydroxide slurry is previously added. The ratio of hydrolysate solution to magnesium hydroxide slurry added to the reactor is based on titration dosage (e.g., 1 ml/min of base slurry to 20 ml/min of hydrolysate). The resultant mixture is then pumped to one or more additional CSTRs. Additional base slurry is added to each successive CSTR reactor if the pH of the mixture fell below a certain level. Retention time in each reactor is constrained by fixing the target volume and maintaining a target flow rate (where rate multiplied by volume equals the retention time). To prevent build-up of foam, antifoam is also delivered into one of the stirred tank reactors. The table below describes operating planned operating ranges at laboratory bench scale using two CSTR reactors in series.

| Parameter | Operating Ranges |
|---|---|
| Hz pump rate | 10-95 ml/min |
| Antifoam pump rate | 0.1-0.5 ml/min |
| Retention volume reactor 1 | 400-4000 ml |
| Retention volume reactor 2 | 500-4000 ml |
| Total retention time | 30-300 min |
| Total base pump rate | 0.1-20 ml/min |
| Total output flow rate | 20-100 ml/min |

5.4. Example 4

Relationship Between Temperature and pH in Hydrolysate Detoxification with Magnesium Hydroxide A hydrolysate obtained from energy cane (DP 100513-1) was subjected to the detoxification procedure described in Section 5.2.1.3. using varying amounts of magnesium hydroxide at temperatures of 50° C., 70° C. and 90° C., respectively. Table 3 depicts the pH of the reaction as a function of temperature of the hydrolysate following addition of 142.5 magnesium hydroxide/1 kg hydrolysate. As indicated in Table 3, the pH of the hydrolysate solution decreases as the temperature of the solution is increased.

TABLE 3

Effect of Temperature on pH in Detoxification of Lignocellulosic Hydrolysates with Magnesium Hydroxide

| Temperature (° C.) | Reaction Time (h) | Dosage (g Mg(OH)$_2$/kg hydrolysate) | pH |
|---|---|---|---|
| 50 | 4 | 142.5 | 7.73 |
| 70 | 4 | 142.5 | 7.24 |
| 90 | 4 | 142.5 | 6.87 |

5.5. Example 5

Fermentation of Detoxified Hydrolysates 5.5.1. Materials and Methods

Following the detoxification and acidification, the hydrolysate solutions were fermented to produce ethanol. Fermentations of detoxified hydrolysate were conducted using *E. coli* as ethanologen at 35° C. Fermentation was carried out in minimal media with or without additional nutrient such as vitamins and CSL at starting pH between 5.0 and 7.0 with or without pH control.

Processes include fermentation by Erlenmeyer flask, Fleaker (Spectrum Lab), DasGip fedbatch-pro (DasGip technology), 2 L BioFlo fermenter (New Brunswick), and 10 L fermenter (B. Braun Biotech). Batch and fed-batch fermentations were conducted in 2 L and 10 L fermenters. E. coli inoculum cultures were grown in three steps. Seed I and II media consist of 40 mM MES, 1×AM6 (0.5 g/L sodium phosphate, 0.859 g/L urea), 1% CSL, and 60.79 g/L glucose. A 250 ml Erlenmeyer flask containing 100 ml medium was inoculated with 100 µl glycerol stock, and grown for 11 hours at 35° C. on a rotary shaker at 120 rpm (seed I). Seed II culture was inoculated with 100 µl of seed I culture, and grown for 11 hours at 35° C. on a rotary shaker at 120 rpm. Seed III culture containing 1×AM6, 5 g/L CSL, 50% detoxified hydrolysate (v/v), and 0.6% yeast autolysate was inoculated with 5% seed II culture in 2 L fermenter and grown at 35° C. (pH of 7) with agitation at 495 rpm for 10-11 hours until the ethanol concentration reached 5 g/L. The main fermentation vessel containing 95% (v/v) detoxified hydrolysate and 1×AM6 with or without additional nutrient was inoculated with 5% (v/v) seed III inoculum, and aerobic fermentation was carried out in both batch and fed-batch modes at 35° C. (pH of 7). During fed-batch fermentation, detoxified hydrolysate and AM6 were fed at various rates using a dissolved oxygen cascade control strategy by agitation ramping profile to maintain dissolved oxygen during feeding.

Ethanol concentrations from fermentation samples were determined using gas chromatography (GC, Agilent 6890 series). In particular, an Agilent system with a flame ionization detector and a HP-Innowax column was used. The GC system settings include 1) an HP-INNOWax polyethylene glycol capillary column (30 m×0.25 mm×0.25 um); 2) helium as carrier gas at 0.8 mL/min constant flow; 3) oven program: 40° C. (hold for 5.6 min), ramp 25° C./min to 125° C.; 4) injection: inlet temperature 250° C., injection volume 1 uL with a split ratio of 100:1. The compound 1-propanol was used as internal standard and a multi-point standard curve was obtained to calculate the final ethanol concentration for each sample. Samples were diluted with methanol containing 0.2% 1-propanol as an internal standard and injected into GC system after removal of precipitates. Ethanol was identified by retention time and quantified by peak area.

5.5.2. Results

The ability of the ethanologen to manufacture ethanol, defined as fermentability, was assessed for detoxified hydrolysates following detoxification with magnesium hydroxide or with calcium hydroxide. Detoxification reactions with calcium hydroxide were run under standard overliming conditions (55° C. for 30 minutes) in similar fashion to detoxification reactions described in Example 2.

The results for fermentability of the detoxified hydrolysates are shown in Table 4. In Table 4, the fermentability metric has been normalized to standard overliming conditions, where a fermentability of 1 is defined as a condition that reaches the same maximal ethanol concentration as the standard overliming condition. As shown in Table 4, the hydrolysates detoxified with magnesium hydroxide shows slightly lower fermentability in E. coli compared to the overliming control. Accordingly, detoxification with magnesium hydroxide produces hydrolysates that are readily fermented by ethanologens, producing high yields of ethanol. The quantity of ethanol produced is comparable to that of hydrolysates that are detoxified with calcium hydroxide.

TABLE 4

Fermentability of Detoxified Hydrolysates

| | | | Ethanol Production | |
| --- | --- | --- | --- | --- |
| Hydrolysate Name | Biomass | Ethanologen | Fermentability normalized to overliming condition | Max ethanol rate (g EtOH/L/hr) |
| DP 100309 | sorghum | E. coli (BD28512) | 0.88 | 0.9 |
| DP 100511 | energy cane | E. coli (BD28512) | 0.92 | 0.86 |
| DP 100513-1 | energy cane | E. coli (BD28512) | 0.88 | 0.9 |

5.6. Example 6

Generation of Titration Curves 5.6.1. Materials and Methods

Titration curves for the addition of three different bases (magnesium hydroxide, calcium hydroxide and sodium hydroxide) added to hydrolysate DP 110105, derived from sugar cane, were generated to determine the amount of base that can be added to raise the pH of the hydrolysate solution to a particular levels. To generate titration curves, a preheated, pre-weighed quantity of hydrolysate DP 110105, was treated with stirring with periodic additions of aliquots of the labeled base or base slurry, and the pH after each addition of base aliquot was recorded. The base additions were done via manual pipette, buret, peristaltic pump, or a syringe pump to either a beaker with stir bar pre-charged with hydrolysate or an overhead stirred tank reactor pre-charged with hydrolysate. A plot was created of these pH values with volume of base used as the abscissa and the pH value as the ordinate.

5.6.2. Results

Figure 3:
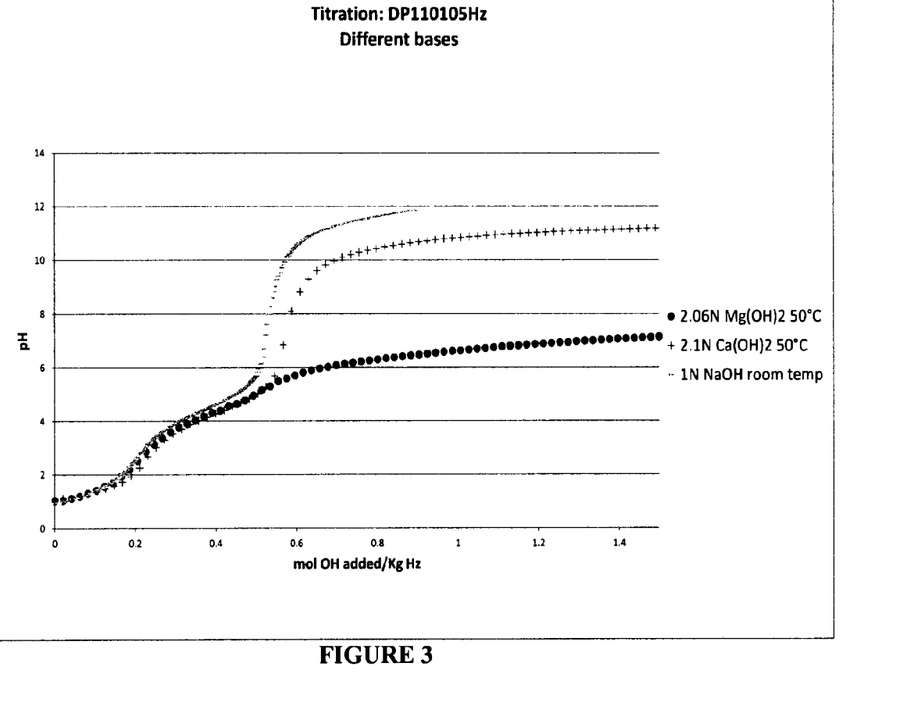
FIG. 3: Titration curves of a hydrolysate obtained from a sugar cane biomass using three different bases.

The titration curves of the three bases are shown in FIG. 3. Addition of increasing amounts of magnesium hydroxide to the hydrolysate solution resulted in a slow rise of the pH up to a maximum pH of less than 8. Addition of calcium hydroxide or sodium hydroxide resulted in a precipitous rise in pH as the base was added.

For calcium hydroxide addition, the pH levels off at a value greater than 10. The titration studies indicate that magnesium hydroxide has a low solubility in the hydrolysate solution, particularly at a pH in the range of 6 to 8, where the detoxification process is performed. Therefore, the quantity of hydroxide ion in the hydrolysate solution available to react with the compounds of the hydrolysate (e.g., total fermentable sugars and furan aldehydes) is limited when magnesium hydroxide is used as a detoxification base, particularly when compared to calcium hydroxide or sodium hydroxide.

5.7. Example 7

Kinetic Studies for Detoxification with Magnesium Hydroxide 5.7.1. Materials and Methods To analyze the kinetics of the detoxification process, the methods described in Example 2 using hydrolysate DP 100513 with magnesium hydroxide as a detoxification base were run at various temperatures, pH levels, and concentrations of the hydrolysate. Samples were taken at time points after the addition of base or base slurry and characterized for concentration of various analytes. The time-dependent decreases in concentration of xylose and furfural were selected to represent the broader competition between furans and aldoses, as these two compounds were present in the highest concentration in the starting hydrolysate and thus were most amenable to good model fits. These data were fit to the general form of the Arrhenius equation assuming power law kinetics to solve for the pre-exponential factor, orders of reaction and activation energies. The model process was an iterative minimization of the sums of squares for the errors such that all data could be fit to a single equation for each parameter. Various nonlinear fitting software was used, including Excel SOLVER and Athena. The activation energy for the furfural removal equation was lower than that for xylose elimination, which is consistent with the higher selectivity for furfural destruction at lower temperatures observed.

5.7.2. Results

Results from the kinetic study indicate that the activation energy of furfural elimination is lower than the activation energy for xylose degradation. As a result, higher selectivity is achieved at lower temperatures.

6. SPECIFIC EMBODIMENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of reducing the toxicity of a lignocellulosic hydrolysate towards a fermenting organism, or for reducing at least a portion of one inhibitor to a fermenting organism from a lignocellulosic hydrolysate, comprising the step of mixing a starting lignocellulosic hydrolysate solution, said starting lignocellulosic hydrolysate solution comprising a mixture of fermentable sugars, furan aldehydes and aliphatic acids, with a magnesium base selected from magnesium hydroxide, magnesium carbonate and magnesium oxide in an amount of 2 g/1 kg hydrolysate to 200 g/1 kg hydrolysate, at a pH of 6.2 to 9.5 and a temperature of 30° C. and 60° C. for a period of time, that results in the formation of a detoxified hydrolysate solution comprising at least 90% of the total fermentable sugars present in the starting lignocellulosic hydrolysate solution and no greater than 40% of furan aldehydes present in the starting lignocellulosic hydrolysate solution, thereby reducing the toxicity of the lignocellulosic hydrolysate.

2. The method of claim 1, wherein the magnesium base is magnesium hydroxide.

3. The method of claim 1, wherein the magnesium base is magnesium carbonate.

4. The method of claim 1, wherein the magnesium base is magnesium oxide.

5. The method of claim 1, wherein said conditions include a temperature of between 40° C. and 60° C.

6. The method of claim 1, wherein said conditions include a temperature of between 45° C. and 50° C.

7. The method of claim 1, wherein said conditions include a pH in the range from 6.5 to 8.

8. The method of claim 1, wherein mixing the starting hydrolysate with the magnesium base is carried out in a batch reactor.

9. The method of claim 1, wherein mixing the starting hydrolysate with the magnesium base is carried out in a continuous reactor.

10. The method of claim 9, wherein the continuous reactor is a plug flow reactor (PFR).

11. The method of claim 9, wherein the continuous reactor is a continuous stirred tank reactor (CSTR).

12. The method of claim 1, wherein mixing the starting hydrolysate with the magnesium base is carried out for a period of time between 1 hour and 40 hours.

13. The method of claim 1, wherein mixing the starting hydrolysate with the magnesium base is carried out for a period of time between 2 hours and 12 hours.

14. The method of claim 1, wherein mixing the starting hydrolysate with the magnesium base is carried out for a period of time between 3 hours and 9 hours.

15. The method of claim 1, wherein the concentration of total fermentable sugars in the starting hydrolysate is between 30 g/L and 160 g/L.

16. The method of claim 1, wherein the concentration of total fermentable sugars in the starting hydrolysate is between 40 g/L and 95 g/L.

17. The method of claim 1, wherein the concentration of total fermentable sugars in the starting hydrolysate is between 50 g/L and 70 g/L.

18. The method of claim 1, wherein the furan aldehydes are comprised of furfural and 5-hydroxymethyl furfural (5-HMF).

19. The method of claim 18, wherein the starting concentration of furfural in the starting hydrolysate is between 0.5 g/L and 10 g/L.

20. The method of claim 18, wherein the starting concentration of furfural in the starting hydrolysate is between 1.5 g/L and 5 g/L.

21. The method of claim 18, wherein the concentration of 5-HMF in the starting hydrolysate is between 0.1 g/L and 5 g/L.

22. The method of claim 18, wherein the concentration of 5-HMF in the starting hydrolysate is between 0.5 g/L and 2.5 g/L.

23. The method of claim 1, wherein the aliphatic acids are comprised of acetic acid and lactic acid.

24. The method of claim 23, wherein the concentration of acetic acid in the starting hydrolysate is between 2 g/L and 17 g/L.

25. The method of claim 23, wherein the concentration of acetic acid in the starting hydrolysate is between 11 g/L and 16 g/L.

26. The method of claim 23, wherein the concentration of lactic acid in the starting hydrolysate is between 0 g/L and 12 g/L.

27. The method of claim 1, wherein the starting hydrolysate further comprises phenolics.

28. The method of claim 27, wherein the concentration of phenolics in the starting hydrolysate is between 0.5 g/L and 5 g/L.

29. The method of claim 1, wherein the fermentable sugars include one or more of xylose, arabinose, rhamnose, glucose, mannose and galactose.

30. The method of claim 1, wherein the detoxified hydrolysate solution comprises no greater than 30% of furan aldehydes present in the starting lignocellulosic hydrolysate solution.

31. The method of claim 1, wherein the detoxified hydrolysate solution comprises no greater than 20% of furan aldehydes present in the starting lignocellulosic hydrolysate solution.

32. The method of claim 1, wherein the detoxified hydrolysate solution comprises no greater than 10% of furan aldehydes present in the starting lignocellulosic hydrolysate solution.

33. The method of claim 1, wherein the detoxified hydrolysate solution comprises at least 90% of the total fermentable sugars present in the starting hydrolysate solution.

34. The method of claim 1, wherein the detoxified hydrolysate solution comprises at least 93% of the total fermentable sugars present in the starting hydrolysate solution.

35. The method of claim 1, wherein the detoxified hydrolysate solution comprises at least 95% of the total fermentable sugars present in the starting hydrolysate solution.

36. The method of claim 1, wherein the detoxified hydrolysate solution comprises at least 99% of the total fermentable sugars present in the starting hydrolysate solution.

37. The method of claim 1, wherein the amount of magnesium base added to the hydrolysate solution is between 40 g/1 kg hydrolysate to 160 g/1 kg hydrolysate.

38. The method of claim 1, further comprising the step of adding an acid to lower the pH of the detoxified hydrolysate to a pH of between 3.5 and 8.

39. The method of claim 1, further comprising the step of adding an acid to lower the pH of the detoxified hydrolysate to a pH of between 4 and 7.

40. The method of claim 1, wherein the starting hydrolysate solution is prepared by hydrolyzing a lignocellulosic biomass.

41. The method of claim 40, wherein the lignocellulosic biomass is selected from Napier grass, energy cane, sorghum, giant reed, sugar beet, switchgrass, bagasse, rice straw, miscanthus, switchgrass, wheat straw, wood, wood waste, paper, paper waste, agricultural waste, municipal waste, birchwood, oat spelt, corn stover, eucalyptus, willow, hybrid poplar, short-rotation woody crop, conifer softwood and crop residue.

42. The method of claim 1, further comprising the step of concentrating a hydrolysate solution to produce said starting hydrolysate solution prior to said mixing step.

* * * * *